United States Patent
Akui et al.

(10) Patent No.: US 11,992,187 B2
(45) Date of Patent: May 28, 2024

(54) ENDOSCOPE

(71) Applicant: OLYMPUS CORPORATION, Tokyo (JP)

(72) Inventors: Nobuaki Akui, Hino (JP); Hidetoshi Saito, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 600 days.

(21) Appl. No.: 17/122,317

(22) Filed: Dec. 15, 2020

(65) Prior Publication Data

US 2021/0127950 A1     May 6, 2021

Related U.S. Application Data

(63) Continuation of application No. PCT/JP2018/026195, filed on Jul. 11, 2018.

(51) Int. Cl.
*A61B 1/00* (2006.01)
*A61B 1/005* (2006.01)
(Continued)

(52) U.S. Cl.
CPC ........ *A61B 1/0051* (2013.01); *A61B 1/00087* (2013.01); *A61B 1/018* (2013.01); *A61B 1/0661* (2013.01)

(58) Field of Classification Search
CPC ... A61B 1/0051; A61B 1/00087; A61B 1/018; A61B 1/0661; A61B 1/00; A61B 1/01;
(Continued)

(56) References Cited

U.S. PATENT DOCUMENTS

| | | | |
|---|---|---|---|
| 6,179,776 B1 | 1/2001 | Adams et al. | |
| 2008/0021274 A1* | 1/2008 | Bayer | A61B 1/00101 600/117 |

(Continued)

FOREIGN PATENT DOCUMENTS

| | | |
|---|---|---|
| JP | 05-184535 A | 7/1993 |
| JP | 2002-538873 A | 11/2002 |

(Continued)

OTHER PUBLICATIONS

International Search Report dated Sep. 4, 2018 received in PCT/JP2018/026195.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An endoscope includes an insertion portion, a distal end rigid member, and a channel tube. The distal end rigid member is provided on a distal end side with respect to the bending portion of the insertion portion, and includes an illumination window, an observation window, and a treatment instrument opening. As the distal end rigid member moves relative to the bending portion in a distal end direction of a longitudinal axial direction, the distal end rigid member can change from a first state in which a distance between a proximal end surface of the distal end rigid member and a distal end surface of the bending portion is fixed to a first distance to a second state in which the distance is equal to a second distance longer than the first distance.

19 Claims, 15 Drawing Sheets

(51) Int. Cl.
*A61B 1/018* (2006.01)
*A61B 1/06* (2006.01)

(58) Field of Classification Search
CPC . A61B 1/0058; A61B 1/0008; A61B 1/00097;
A61B 1/0055; A61B 1/0125; A61B 1/005
USPC ........................................................ 600/146
See application file for complete search history.

(56) References Cited

U.S. PATENT DOCUMENTS

| | | | | |
|---|---|---|---|---|
| 2009/0088601 | A1* | 4/2009 | Doguchi | A61B 1/015 |
| | | | | 600/104 |
| 2010/0121269 | A1* | 5/2010 | Goldenberg | A61M 25/0105 |
| | | | | 604/95.01 |
| 2011/0092766 | A1* | 4/2011 | Monassevitch | A61B 1/00135 |
| | | | | 600/104 |
| 2013/0184528 | A1* | 7/2013 | Onuki | A61B 17/062 |
| | | | | 600/146 |
| 2016/0213225 | A1* | 7/2016 | Sato | A61B 1/005 |
| 2016/0287055 | A1* | 10/2016 | Kesten | A61M 25/10 |

FOREIGN PATENT DOCUMENTS

| | | |
|---|---|---|
| JP | 2004-141486 A | 5/2004 |
| JP | 2010-172513 A | 8/2010 |
| JP | 2011-200428 A | 10/2011 |
| WO | 00/54653 A1 | 9/2000 |
| WO | 2017/104279 A1 | 6/2017 |

* cited by examiner

ENDOSCOPE

CROSS REFERENCE TO RELATED APPLICATION

This application is a continuation application of PCT/JP2018/026195 filed on Jul. 11, 2018, the entire contents of which are incorporated herein by this reference.

BACKGROUND OF THE INVENTION

1. Field of the Invention

The present invention relates to an endoscope including an insertion portion including a bending portion.

2. Description of the Related Art

Endoscopes have been widely used in medical and industrial fields. An endoscope includes an elongated insertion portion, and an observation window is provided at a distal end portion of the insertion portion. A user of the endoscope, such as an operator can perform examination, treatment, or the like with the endoscope by causing a display device to display an endoscope image based on an object image incident through the observation window.

The bending portion is provided at the proximal end of the distal end portion of the insertion portion, and the user of the endoscope can bend the bending portion in a predetermined direction by operating a bending operation member provided to an operation portion of the endoscope. Thus, while viewing the endoscope image, the user can push the insertion portion in and bend the bending portion to move the distal end portion of the insertion portion closer to a desired site in a subject.

In some endoscope, a treatment instrument insertion channel is provided at the insertion portion. For example, Japanese Patent Application Laid-Open Publication No. 2011-200428 discloses an endoscope in which the bending portion is bendable in two directions and the treatment instrument insertion channel is provided to the insertion portion. The user can insert a treatment instrument into the treatment instrument insertion channel, cause a distal end portion of the treatment instrument to protrude through a treatment instrument opening of the distal end portion of the insertion portion, and perform treatment with the treatment instrument.

SUMMARY OF THE INVENTION

An endoscope according to an aspect of the present invention includes: an insertion portion that is a tubal member extended in a longitudinal axial direction; a channel tube that is disposed in the insertion portion and into which a treatment instrument can be inserted; a bending portion provided to the insertion portion; and a distal end rigid member that is provided on a distal end side with respect to the bending portion of the insertion portion and includes an illumination window through which a subject is illuminated, an observation window configured such that light for image pickup of the subject is incident on the observation window, and a treatment instrument opening connected with the channel tube. As the distal end rigid member moves relative to the bending portion in a distal end direction of the longitudinal axial direction, the distal end rigid member can change from a first state in which a distance between a proximal end surface of the distal end rigid member and a distal end surface of the bending portion is fixed to a first distance to a second state in which the distance between the proximal end surface of the distal end rigid member and the distal end surface of the bending portion is equal to a second distance longer than the first distance.

An endoscope according to another aspect of the present invention includes: an insertion portion that is a tubal member extended in a longitudinal axial direction; a channel tube that is disposed in the insertion portion and into which a treatment instrument can be inserted; a bending portion provided to the insertion portion; and a distal end rigid member that is provided on a distal end side with respect to the bending portion of the insertion portion and includes an illumination window through which a subject is illuminated, an observation window configured such that light for image pickup of the subject is incident on the observation window, and a treatment instrument opening connected with the channel tube. As the distal end rigid member moves relative to the bending portion in a distal end direction of the longitudinal axial direction, the distal end rigid member is movable from a first fixation position where the distal end rigid member is fixed to the bending portion to a second fixation position where the distal end rigid member separates further from the bending portion than the first fixation position.

DETAILED DESCRIPTION OF THE PREFERRED EMBODIMENTS

Figure 1:
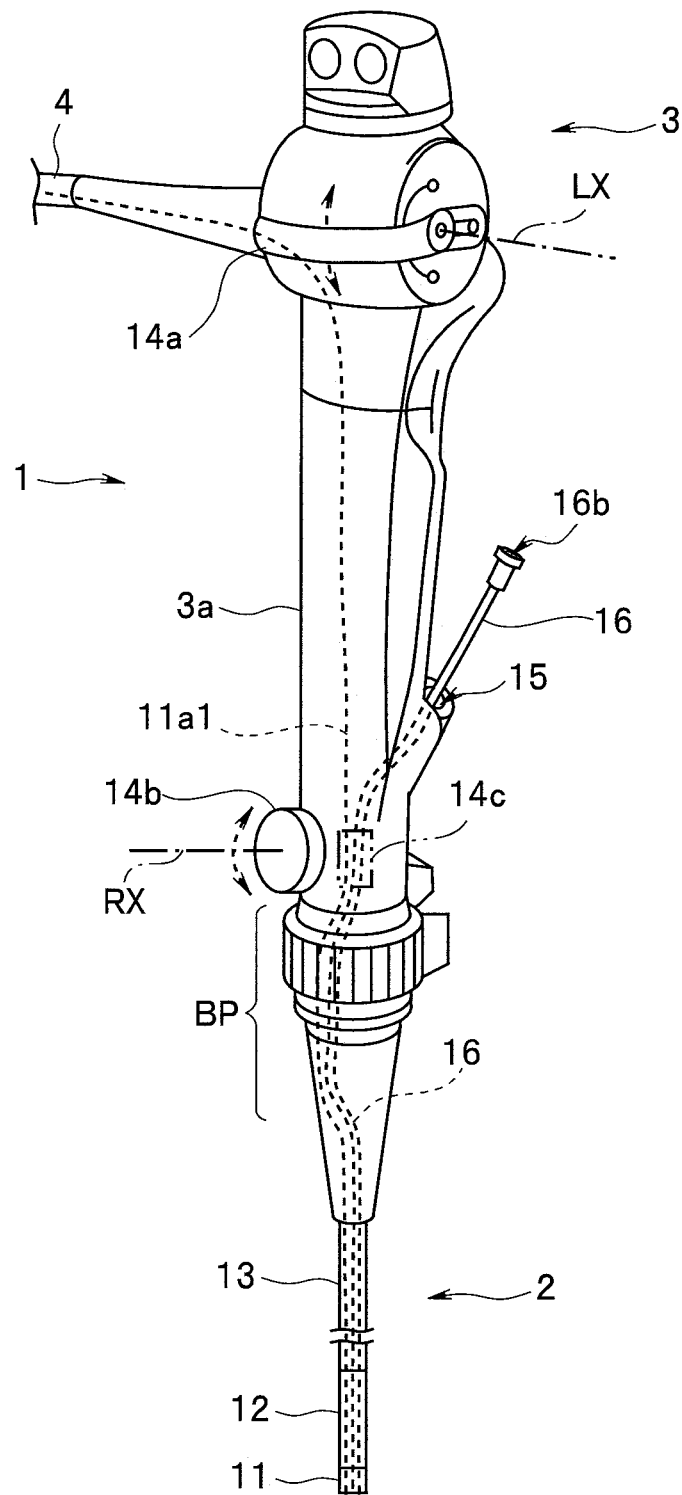
FIG. 1 is a configuration diagram of an endoscope according to a first embodiment of the present invention.

The present invention will be described below with reference to embodiments.

Note that in each drawing used in the following description, a different scale is applied to each component so that the component has a size recognizable in the drawing, and the present invention is not limited to the number of components, the shape of each component, the ratio of sizes of the components, and the relative positional relation among the components illustrated in the drawings.

First Embodiment

Figure 2:
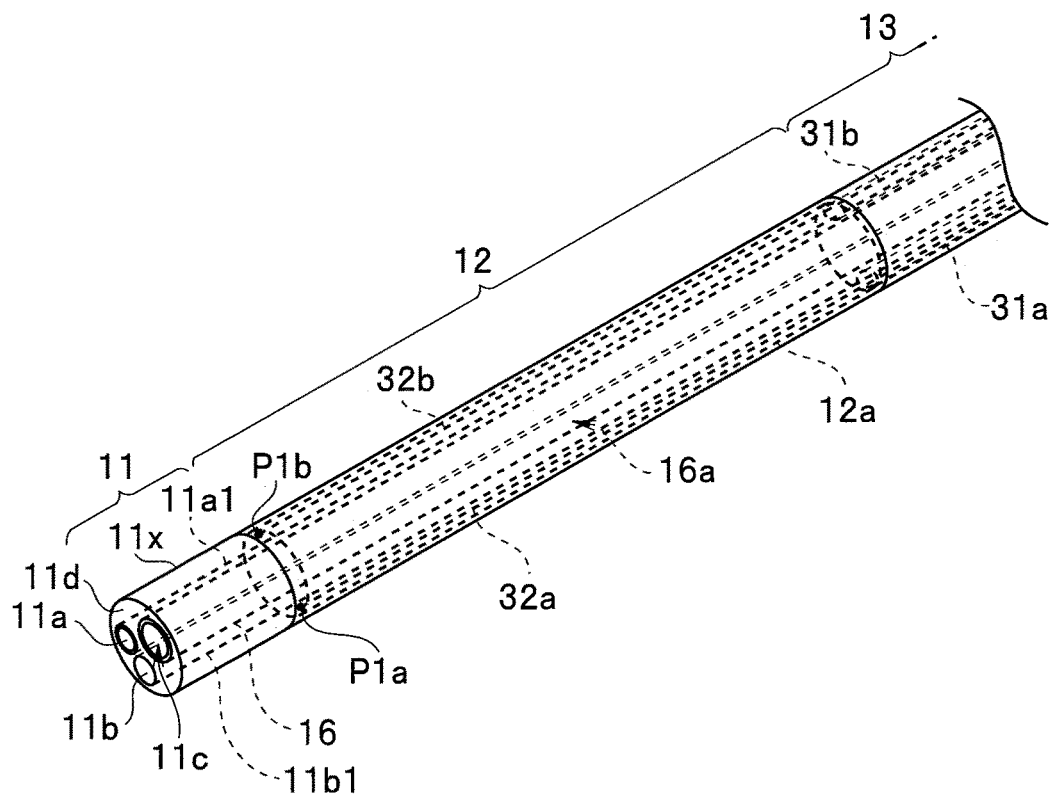
FIG. 2 is a perspective view of a distal end portion of an insertion portion according to the first embodiment of the present invention.

FIG. 1 is a configuration diagram of an endoscope according to an embodiment of the present invention. FIG. 2 is a perspective view of a distal end portion of an insertion portion according to the embodiment of the present invention.

An endoscope 1 includes an elongated insertion portion 2, an operation portion 3 connected with the proximal end of the insertion portion 2, and a universal cable 4 extending from the operation portion 3. A connector (not illustrated) for connection with a main device such as a video processor is provided at the distal end of the universal cable 4.

The insertion portion 2 includes, sequentially from the distal end, a distal end portion 11, a bending portion 12, and a flexible tube portion 13. The insertion portion 2 is inserted into a subject. In other words, the bending portion 12 is provided to the insertion portion 2 that is inserted into the subject.

The distal end portion 11 includes a distal end rigid member 11x of a cylinder shape. The distal end rigid member 11x has three holes formed in the longitudinal axial direction of the insertion portion 2 as described later (refer to FIG. 5). As illustrated in FIG. 2, the distal end portion 11 includes an observation window 11a, an illumination window 11b, and a treatment instrument opening 11c corresponding to the three holes, respectively. An object is irradiated with illumination light emitted from the illumination window 11b. Reflected light of the illumination light from the object is incident on the observation window 11a.

A distal end surface of an elongated image guide 11a1 for an optical fiber bundle is disposed behind the observation window 11a. The image guide 11a1 can transmit light of an object image. Thus, an objective optical system such as a lens is disposed at the distal end of the image guide 11a1, and a distal end portion of the objective optical system configures the observation window 11a.

The image guide 11a1 is inserted into the insertion portion 2, the operation portion 3, and the universal cable 4. A proximal end portion of the image guide 11a1 is connected with the connector connected with a distal end portion of the universal cable 4. When the connector of the universal cable 4 is connected with the video processor, light emitted from a proximal end surface of the image guide 11a1 is incident on a light-receiving surface of an image pickup device in the video processor.

Note that in this example, the image guide 11a1 is provided behind the observation window 11a, but an image pickup device such as a CMOS image sensor may be provided. In this case, a signal line extending from the image pickup device is inserted into the insertion portion 2, the operation portion 3, and the universal cable 4.

A distal end surface of a light guide 11b1 for an optical fiber bundle is disposed behind the illumination window 11b. The light guide 11b1 is disposed in the insertion portion 2 and can transmit illumination light. Thus, an illumination optical system such as a lens is disposed at the distal end of the light guide 11b1, and a distal end portion of the illumination optical system configures the illumination window 11b.

The elongated light guide 11b1 configures an illumination unit. A proximal end portion of the light guide 11b1 is connected with a connector connected with the distal end portion of the universal cable 4 and guides illumination light from a light source in the video processor. The illumination light is emitted from the illumination window 11b.

Note that in this example, the light guide 11b1 is provided behind the illumination window 11b, but a light-emitting element such as a light-emitting diode (LED) may be provided. In this case, a power supply line extending from the light-emitting element is inserted into the insertion portion 2, the operation portion 3, and the universal cable 4.

The elongated image guide 11a1 configures an image pickup unit. Light of an object image emitted from the proximal end portion of the image guide 11a1 is photoelectrically converted by the image pickup device in the video processor, and accordingly, an image pickup signal is generated. The video processor generates an endoscope image based on the image pickup signal and outputs an image signal to a display device.

Thus, a user of the endoscope 1 can observe the inside of the subject while viewing the endoscope image displayed on the display device.

The bending portion 12 includes a bending mechanism. A bending pipe 12a is disposed in the bending portion 12. The configuration of the bending portion 12 will be described later.

The flexible tube portion 13 has a configuration in which a flex, a braid, and an external skin resin are stacked from the inner side. The flex is a helical pipe as a flexible member having a shape in which a flat plate material is wound in a helical shape. The braid is a metal net pipe. The external skin resin is formed at an outer peripheral part of the braid and partially included between metal strands of the braid. Accordingly, the flexible tube portion 13 has rigidity and flexibility to some extent.

An operation lever 14a is provided as a bending operation member to the operation portion 3. The operation lever 14a is rotatable about a predetermined axis LX of the operation portion 3 as illustrated with dotted-line arrows. The user can bend the bending portion 12 by operating the operation lever 14a.

Note that in the present embodiment, the bending operation member of the operation portion 3 may be a bending knob of a circular plate shape.

A treatment instrument insertion port 15 is provided at the operation portion 3. An elongated channel tube 16 is inserted into the insertion portion 2. An internal path of the channel tube 16 forms a treatment instrument insertion channel 16a into which a treatment instrument can be inserted. For example, the treatment instrument is an elongated laser probe of a laser treatment device.

A proximal end part of the channel tube 16 extends from the treatment instrument insertion port 15 of the operation portion 3. In other words, the treatment instrument insertion port 15 is a protrusion opening for the proximal end part of the channel tube 16. The channel tube 16 is disposed in the operation portion 3 and the insertion portion 2. A distal end part of the channel tube 16 is inserted into a hole of the distal end rigid member 11x of the distal end portion 11, which will be described later. The treatment instrument opening 11c of the distal end portion 11 is an opening at the distal end of the treatment instrument insertion channel 16a.

The treatment instrument insertion channel 16a also functions as a reflux path through which liquid such as normal saline is fed into the subject and the liquid returns from the subject.

As described later, the channel tube 16 and the image guide 11a1 are movable to the distal end side at the distal end portion 11. As the channel tube 16 moves to the distal end side at the distal end portion 11, the proximal end part of the channel tube 16 extending from the treatment instrument insertion port 15 moves toward the treatment instrument insertion port 15 while being pulled into the operation portion 3.

In the operation portion 3, the image guide 11a1 is not extended straight but is deflected. Specifically, the image guide 11a1 is deflected in a predetermined region BP in the operation portion 3 in FIG. 1.

A distal end protrusion portion operation knob (hereinafter also simply referred to as an operation knob) 14b is provided at the operation portion 3. A distal end protrusion portion is the distal end part of the channel tube 16 and a distal end part of the image guide 11a1 as described later.

The operation knob 14b is rotatable about a predetermined axis RX of the operation portion 3 as illustrated with dotted-line arrows. A shaft member of the operation knob 14b is connected with a conversion mechanism 14c to be described later.

The user can cause the observation window 11a and the treatment instrument opening 11c to protrude and retract from a distal end surface 11d of the distal end portion 11 by operating the operation knob 14b. As described later, the user can cause the image guide 11a1 and the channel tube 16 to protrude from a distal end surface 14d of the distal end portion 11 by operating the operation knob 14b.

Thus, the user can bend the bending portion 12 in a predetermined direction by operating the operation lever 14a of the operation portion 3. For example, the user operates the operation lever 14a with fingers of the left hand while grasping the insertion portion 2 with the right hand and grasping a grasping portion 3a of the operation portion 3 with the left hand.

The user can view the endoscope image and bend the bending portion 12 to move the distal end portion 11 of the insertion portion 2 further into a tract in the subject.

Then, the user can insert a treatment instrument into the treatment instrument insertion channel 16a through an opening 16b of the proximal end part of the channel tube 16, cause the treatment instrument to protrude from the treatment instrument opening 11c of the channel tube 16 protruding from the distal end surface 11d, and perform treatment in the subject. Accordingly, the treatment instrument opening 11c is a treatment instrument protrusion opening configured such that the treatment instrument protrudes.

Figure 3:
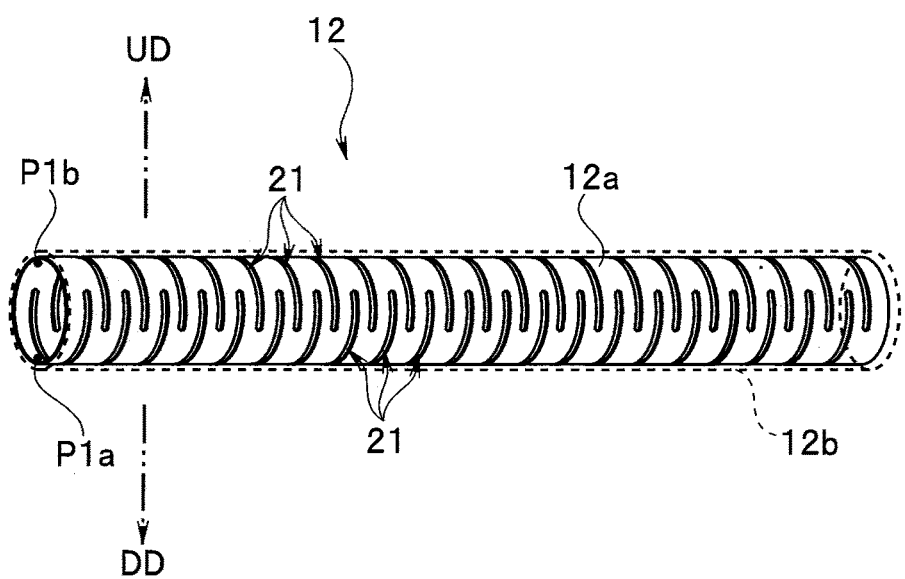
FIG. 3 is a perspective view of a bending pipe disposed in a bending portion according to the first embodiment of the present invention.
Figure 4:
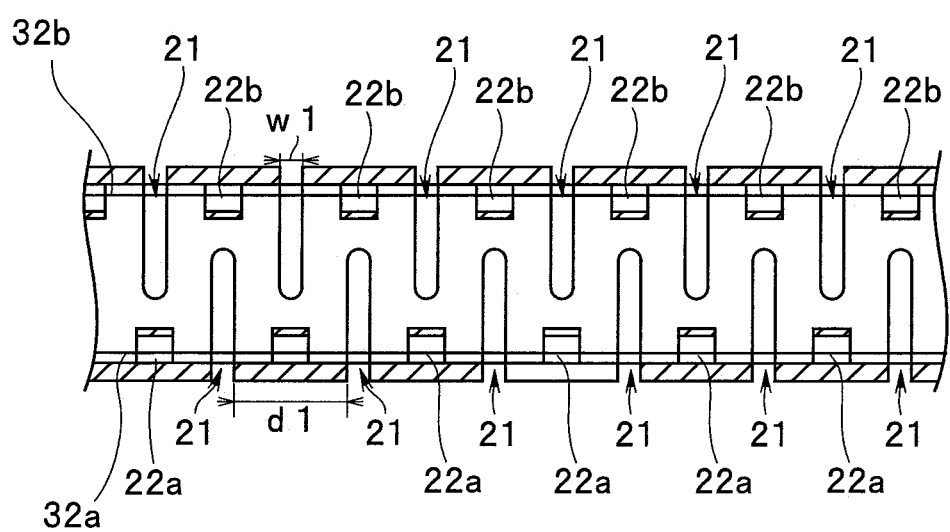
FIG. 4 is a partial cross-sectional view of the bending portion according to the first embodiment of the present invention.

The following describes the configuration of the bending portion 12 with reference to FIGS. 2, 3, and 4.

FIG. 3 is a perspective view of the bending pipe 12a disposed in the bending portion 12. FIG. 4 is a partial cross-sectional view of the bending portion 12.

The bending portion 12 includes the bending pipe 12a. As illustrated in FIG. 3, the bending portion 12 includes the bending pipe 12a and an external skin 12b illustrated with dotted lines. The bending pipe 12a is mainly configured as a cylindrical pipe member formed of superelastic alloy. Examples of superelastic alloy materials configuring the bending pipe 12a include Ni—Ti (nickel titanium), titanium alloy, beta titanium, pure titanium, 64 titanium, A7075, and aluminum alloy.

A plurality of bending slits 21 each having a partially arc shape, penetrating from the outer peripheral surface side to the inner peripheral surface side of the bending pipe 12a, and extending in the circumferential direction of the bending pipe 12a are provided to the bending pipe 12a at a predetermined interval in a longitudinal axial direction by, for example, laser fabrication.

Each bending slit 21 has a width w1 in the longitudinal axial direction of the bending pipe 12a. The plurality of bending slits 21 are formed in a staggered manner at positions on one side and the other side in a direction orthogonal to the longitudinal axial direction of the bending pipe 12a.

Specifically, in the bending pipe 12a, a plurality of bending slits 21 opened in the same direction are arrayed in line at an interval d1 in the longitudinal axial direction of the bending pipe 12a on one side of the bending pipe 12a, which corresponds to an upper side in a bending direction of the bending portion 12.

In addition, in the bending pipe 12a, a plurality of bending slits 21 opened in the same direction are arrayed in line at the interval d1 in a longitudinal direction of the bending pipe 12a on the other side of the bending pipe 12a, which corresponds to a lower side in the bending direction of the bending portion 12.

The bending slits 21 arrayed on one side of the bending pipe 12a are disposed at positions staggered with respect to the bending slits 21 arrayed on the other side of the bending pipe 12a.

Thus, the bending pipe 12a can be bent in a first direction UD on the upper side of the bending portion 12 and in a second direction DD on the lower side of the bending portion 12 in FIG. 3.

As illustrated in FIG. 2, in the flexible tube portion 13 of the insertion portion 2, two coil pipes 31a and 31b made of stainless steel are disposed symmetrically with respect to a central axis CO of the insertion portion 2. A bending wire 32a made of stainless steel is inserted into the coil pipe 31a. A bending wire 32b made of stainless steel is inserted into the coil pipe 31b. A distal end part of each of the coil pipes 31a and 31b is fixed to a distal end part of the flexible tube portion 13 by welding or the like.

As described above, a plurality of coil pipes, the two coil pipes 31a and 31b in this example, as guide members that guide motion of two bending wires are inserted into the flexible tube portion 13.

The bending wires 32a and 32b are one wire, and a central part of the wire is hung on a pulley in the operation portion 3.

The pulley is connected with the operation lever 14a and rotates in accordance with motion of the operation lever 14a.

Thus, as the operation lever 14a rotates about the axis LX of the operation portion 3, one of the bending wires 32a and 32b is pulled to the proximal end side.

As the user moves the operation lever 14a about the axis LX, the bending wires 32a and 32b move in the insertion portion 2 so that one of the bending wires 32a and 32b is pulled and the other is relaxed.

As illustrated in FIG. 4, a plurality of wire guides 22a for the bending wire 32a are provided on the inner peripheral surface of the bending pipe 12a in parallel to the central axis of the bending pipe 12a by welding or the like. A plurality of wire guides 22b for the bending wire 32b are provided on the inner peripheral surface of the bending pipe 12a in parallel to the central axis of the bending pipe 12a.

Each of the wire guides 22a and 22b is made of metal such as stainless steel and is, for example, a ring-shaped member.

Note that the wire guides 22a and 22b may be lance bending portions formed at thin-walled parts of the bending pipe 12a by cutting and bending through press fabrication. Specifically, each lance bending portion is formed by cutting two parallel slits and bending a part between the two slits by pressing. This lance bending portion serves as a wire guide.

The bending wire 32a is inserted into the plurality of wire guides 22a in the bending pipe 12a. The bending wire 32b is inserted into the plurality of wire guides 22b in the bending pipe 12a.

Specifically, the coil pipes 31a and 31b configure a guide member into which the bending wires 32a and 32b are inserted at a position on the proximal end side of the bending portion 12.

The distal end of the bending wire 32a protruding from the distal end of the coil pipe 31a is fixed to the inner peripheral surface of a distal end part of the bending pipe 12a by fixation such as welding. In FIGS. 2 and 3, the distal end of the bending wire 32a is fixed to the bending pipe 12a at the position of a point P1a. Accordingly, the bending wire 32a is inserted across the entire bending portion 12.

Note that the coil pipe 31b into which the bending wire 32b is inserted has a configuration same as the configuration of the coil pipe 31a. As illustrated in FIGS. 2 and 3, the distal end of the bending wire 32b is fixed to the inner peripheral surface of the bending pipe 12a at the position of a point P1b.

When the bending pipe 12a is viewed in a central axial direction of the bending pipe 12a, the point P1a is positioned at a central part of the plurality of lower bending slits 21. When the bending pipe 12a is viewed in the central axial direction of the bending pipe 12a, the point P1b is positioned at a central part of the plurality of upper bending slits 21.

The bending wire 32b is connected with a connection part at the point P1b provided to the bending portion 12 and bends the entire bending portion 12 in a direction opposite to a bending direction by the bending wire 32a by pulling.

When the bending portion 12 is viewed in the longitudinal axial direction of the bending portion 12, the point P1a is positioned on the lower side of the bending portion 12, and the point P1b is positioned on the upper side of the bending portion 12. Connection parts at the points P1a and P1b are positioned at positions symmetric to each other with respect to a longitudinal axis of the bending portion 12.

As described above, the bending wires 32a and 32b are connected with the connection part at the points P1a and P1b, respectively, of the bending portion 12 and bend the entire bending portion 12 in an upward or downward bending direction by pulling.

Note that the above-described bending portion 12 has a structure including the bending pipe 12a in which a plurality of bending slits 21 are formed but may have a structure in which a plurality of annular bending pieces are continuously provided.

The following describes the configuration of the distal end portion 11.

Figure 5:
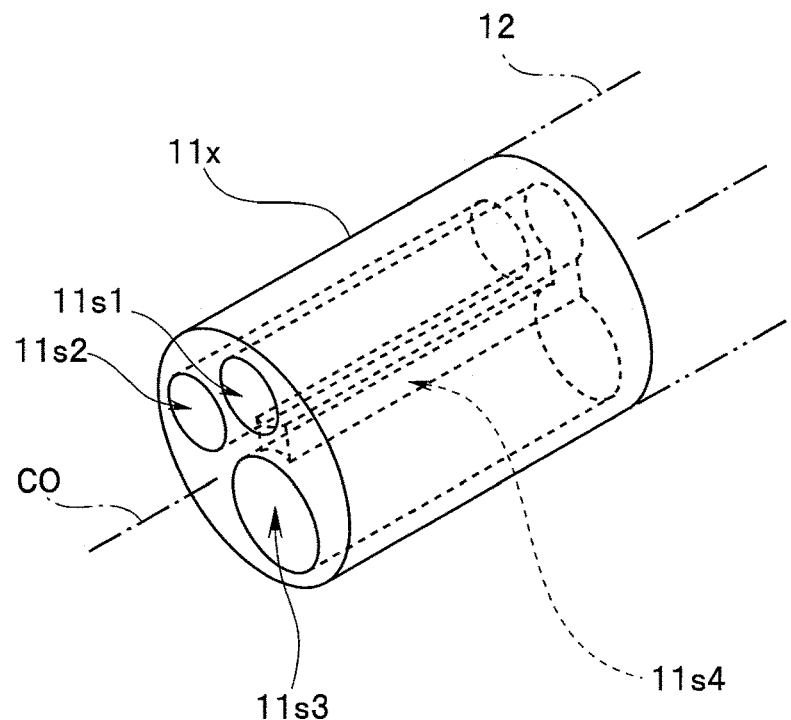
FIG. 5 is a perspective view of a distal end rigid member according to the first embodiment of the present invention.

FIG. 5 is a perspective view of the distal end rigid member 11x.

The distal end rigid member 11x includes three holes 11s1, 11s2, and 11s3 formed along a longitudinal axis of the insertion portion 2. The hole 11s1 is a hole into which the distal end part of the image guide 11a1 as an image pickup unit can be inserted. The hole 11s2 is a hole into which the illumination light guide 11b1 as an illumination unit is inserted. The hole 11s3 is a hole into which the distal end part of the channel tube 16 can be inserted.

The distal end part of the image guide 11a1 is movable in the hole 11s1, and the channel tube 16 is movable in the hole 11s3.

In addition, a slit 11s4 through which the hole 11s1 communicates with the hole 11s3 is formed in the distal end rigid member 11x. The slit 11s4 is formed in an elongated shape from a proximal end surface of the distal end rigid member 11x toward the distal end in the longitudinal axial direction of the insertion portion 2.

Figure 6:
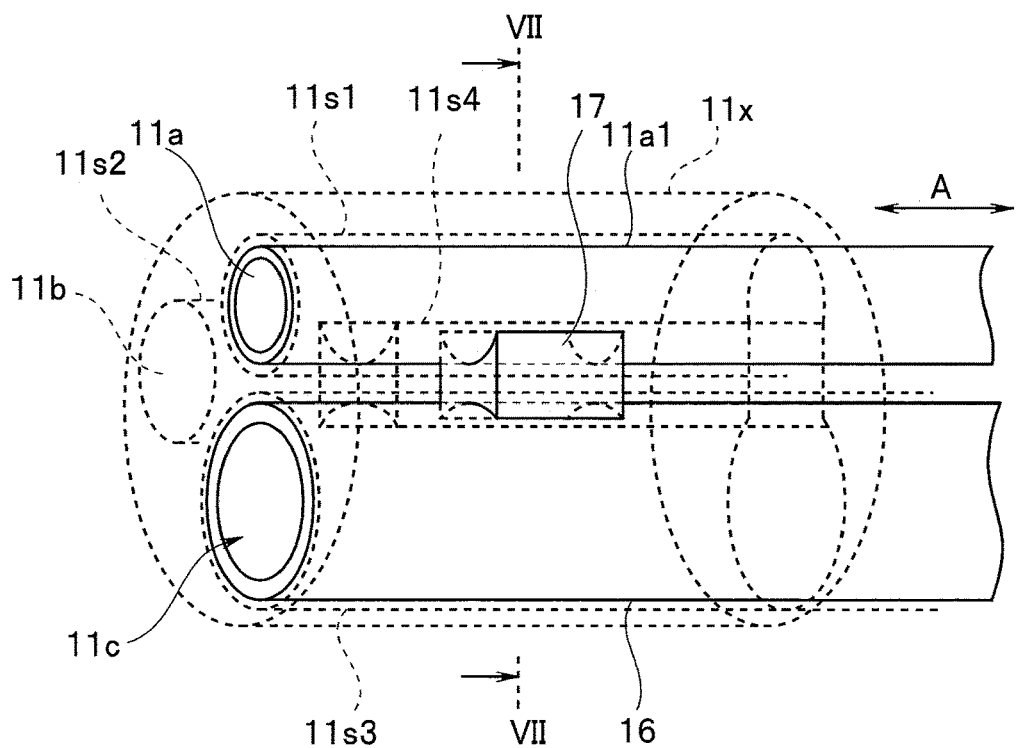
FIG. 6 is a diagram for description of disposition of an image guide and a channel tube in the distal end rigid member according to the first embodiment of the present invention.
Figure 7:
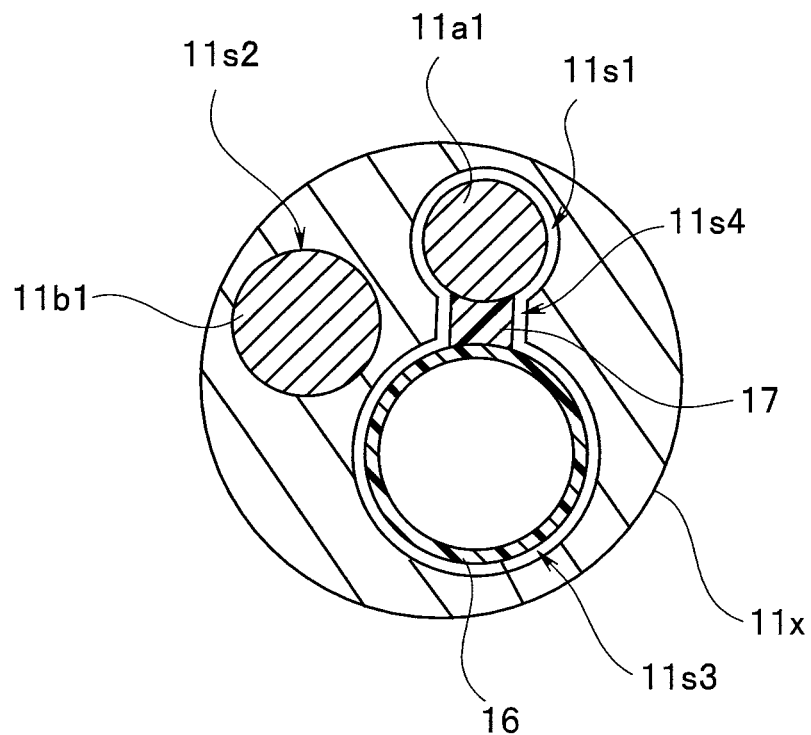
FIG. 7 is a cross-sectional view taken along line VII-VII in FIG. 6.

FIG. 6 is a diagram for description of disposition of the image guide 11a1 and the channel tube 16 in the distal end rigid member 11x. FIG. 7 is a cross-sectional view taken along line VII-VII in FIG. 6.

In FIG. 7, a slanted part in the hole 11s1 is the image guide 11a1. In FIG. 7, a slanted part in the hole 11s2 is the light guide 11b1.

The image guide 11a1 and the channel tube 16 are connected with each other by a connecting member 17. The connecting member 17 is disposed in the slit 11s4 of the distal end rigid member 11x. The connecting member 17 connects the elongated image guide 11a1 including the observation window 11a with the treatment instrument insertion channel tube 16 having the treatment instrument opening 11c at the distal end.

The connecting member 17 is fixed to the image guide 11a1 and the channel tube 16 by a fixation such as a bonding agent. The connecting member 17 is disposed in the slit 11s4 and fixed to the image guide 11a1 and the channel tube 16 so that the connecting member 17 is movable along the longitudinal axis of the insertion portion 2.

Specifically, the connecting member 17 is disposed in the slit 11s4 formed in the longitudinal axial direction of the insertion portion 2 and connects the image guide 11a1 and the channel tube 16. As illustrated with arrows A in FIG. 6, the image guide 11a1 and the channel tube 16 are movable along the longitudinal axis of the insertion portion 2.

Figure 8:
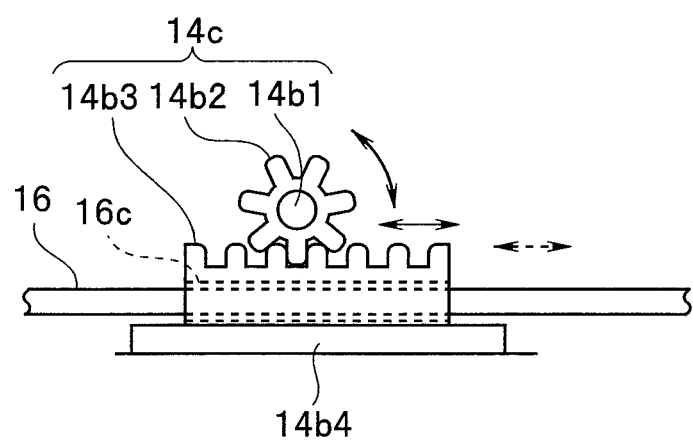
FIG. 8 is a diagram for description of a structure in which the channel tube moves along the central axis of the insertion portion as an operation knob rotates according to the first embodiment of the present invention.

FIG. 8 is a diagram for description of a structure in which the channel tube 16 is moved along a central axis CO of the insertion portion 2 by rotation of the operation knob 14b.

The operation knob 14b as a distal end protrusion portion operation member is rotatable about the axis of a rotation axis member 14b1. The rotation axis member 14b1 is supported in the operation portion 3 by a support member such as a pipe member (not illustrated). The user can move the channel tube 16 along the longitudinal axis of the insertion portion 2 relative to the bending portion 12 by using the operation knob 14b. Specifically, the user can perform, by using the operation knob 14b, movement from a first fixation position at which the distal end rigid member 11x is fixed to the bending portion 12 to a second fixation position at which the distal end rigid member 11x is separated further from the bending portion 12 than the first fixation position.

A pinion gear 14b2 is fixed to one end of the rotation axis member 14b1. A rack 14b3 that is meshed with the pinion gear 14b2 is disposed in the operation portion 3.

The rack 14b3 is supported between the pinion gear 14b2 and a support member 14b4 so that teeth of the rack 14b3 are not removed from the pinion gear 14b2. As illustrated with solid-line arrows in FIG. 8, a plane part of the rack 14b3 and a plane part of the support member 14b4 are slidably in contact with each other so that the rack 14b3 is movable. Accordingly, the rack 14b3 is disposed in the operation portion 3 so that the rack 14b3 is movable in the longitudinal axial direction of the insertion portion 2 in accordance with rotation of the pinion gear 14b2.

The channel tube 16 is fixed to the rack 14b3 by a fixation such as a bonding agent.

Note that an exterior tube 16c for reinforcement may be provided outside the channel tube 16 at least at a part fixed to the rack 14b3 in the channel tube 16 as illustrated with dotted lines in FIG. 8 to reinforce the channel tube 16.

Note that the exterior tube 16c may be provided to cover a range in the channel tube 16 from a vicinity part of the flexible tube portion 13 of the insertion portion 2 to the proximal end part of the channel tube 16.

More specifically, the exterior tube 16c is provided in a range from a part not in the flexible tube portion 13 of the channel tube 16 in the operation portion 3 to a proximal end part protruding from the treatment instrument insertion port 15 of the channel tube 16 when the channel tube 16 is moved to the distal end side in accordance with rotation of the pinion gear 14b2.

Accordingly, in FIG. 8, as the user rotates the operation knob 14b about the axis of the rotation axis member 14b1, the channel tube 16 is moved in the longitudinal axial direction of the insertion portion 2 by the rack-and-pinion configuration of the pinion gear 14b2 and the rack 14b3.

With the above-described exterior tube 16c for reinforcement, it is possible to prevent the channel tube 16 from deflecting and buckling in the operation portion 3 and increase the strength of a part protruding from the treatment instrument insertion port 15 of the channel tube 16, thereby preventing the protruding part from breaking.

Note that the image guide 11a1 is disposed being relaxed in the above-described predetermined region BP in the operation portion 3 as illustrated in FIG. 1 so that the channel tube 16 can be moved in the insertion portion 2 as described later.

The following describes a waterproof structure such as the channel tube 16 in the operation portion 3.

Figure 9:
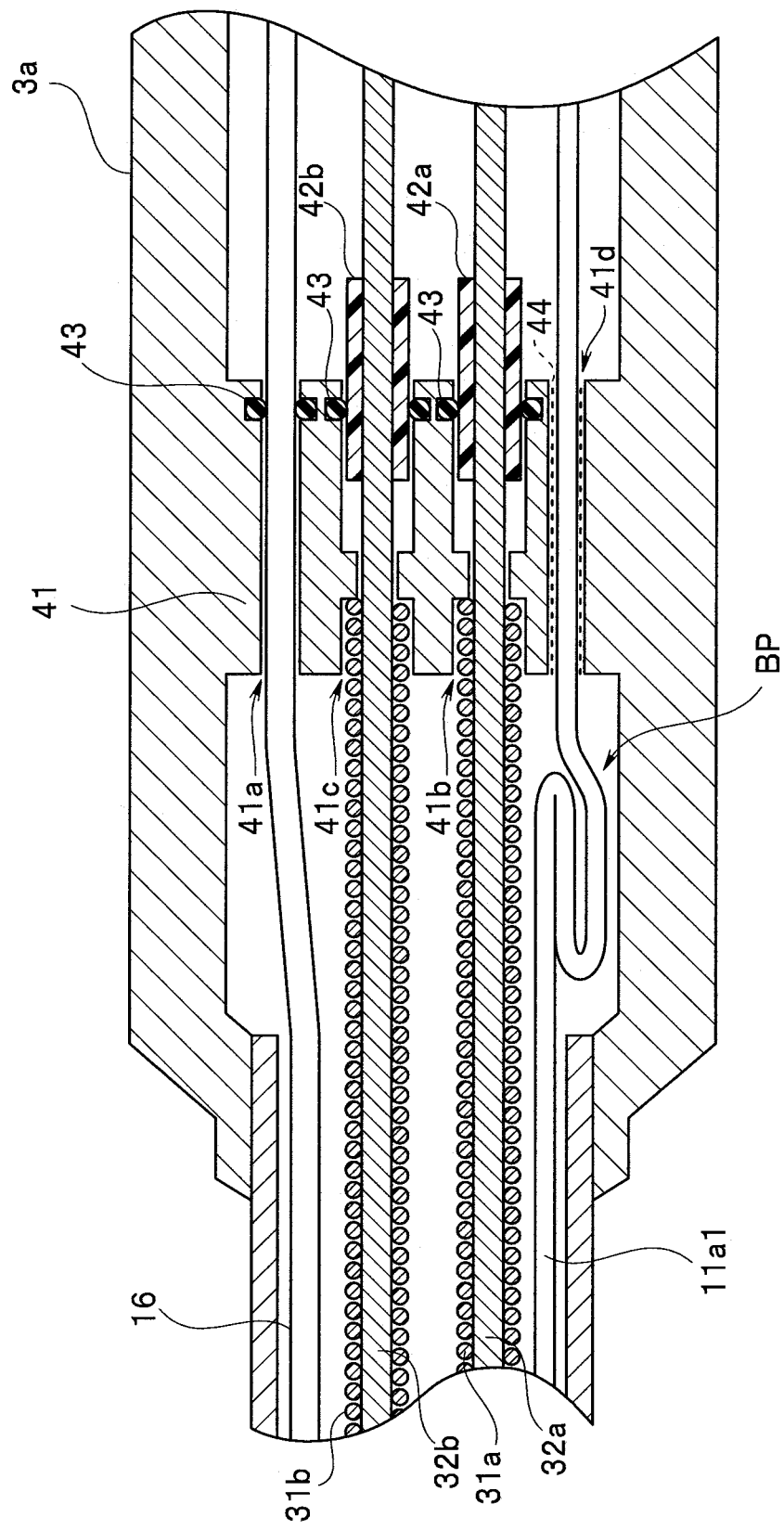
FIG. 9 is a cross-sectional view illustrating a fixed state of internal components in an operation portion according to the first embodiment of the present invention.

FIG. 9 is a cross-sectional view illustrating a fixed state of internal components in the operation portion 3. FIG. 9 illustrates a section along the longitudinal axis of the insertion portion 2.

A partition 41 is provided in the grasping portion 3a of the operation portion 3. A plurality of holes are formed through the partition 41. The channel tube 16 is inserted into one hole 41a. The bending wires 32a and 32b are inserted into other two holes 41b and 41c, respectively. The image guide 11a1 is inserted into another hole 41d.

The bending wires 32a and 32b are inserted into the coil pipes 31a and 31b, respectively, fixed on the distal end side of the partition 41.

The bending wires 32a and 32b are inserted into pipe members 42a and 42b, respectively, on the proximal end side of the partition 41.

The channel tube 16 and the two pipe members 42a and 42b are each inserted into the corresponding one of the holes 41a, 41b, and 41c through an O-shaped ring 43.

The image guide 11a1 is fixed in the hole 41d by a bonding agent 44 illustrated with dotted lines. Although not illustrated, similarly to the image guide 11a1, the light guide 11b1 is fixed in a hole (not illustrated) by the bonding agent 44.

FIG. 9 illustrates that part of the image guide 11a1 is deflected in the region BP.

(Effects)

The following describes protruding and retracting operation of the treatment instrument insertion channel tube 16 in the endoscope 1 described above.

Figure 10:
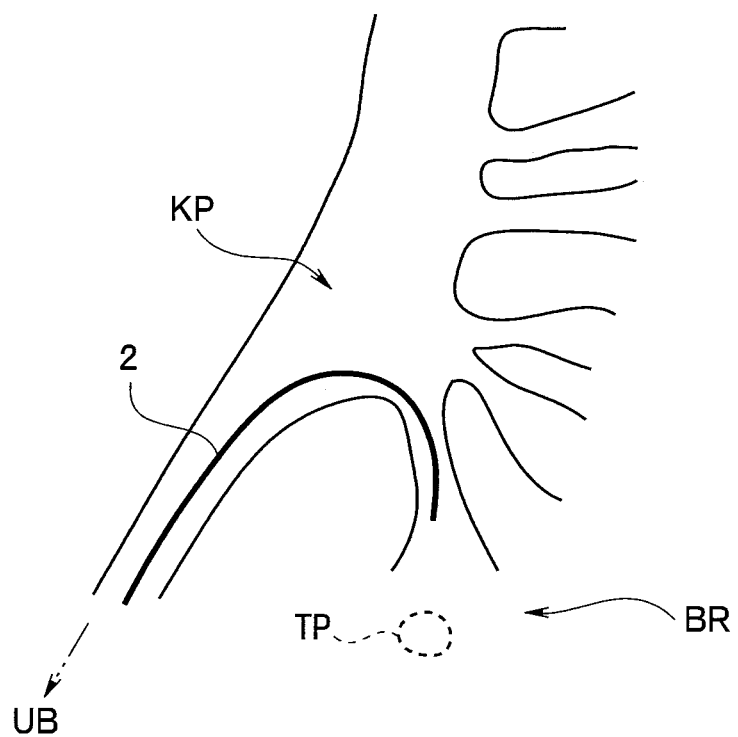
FIG. 10 is a diagram illustrating a state in which the insertion portion of the endoscope is inserted into a subject according to the first embodiment of the present invention.

FIG. 10 is a diagram illustrating a state in which the insertion portion 2 of the endoscope 1 is inserted into the subject. In this example, the insertion portion 2 is inserted into the kidney. The kidney includes a plurality of renal calyces. The insertion portion 2 is inserted through the urethra, passes through the bladder UB, and then enters a renal pelvis KP. An operator can relatively easily move the distal end portion 11 into each renal calyx other than the lower renal calyx BR.

However, as illustrated in FIG. 10, the bending portion 12 needs to be bent into a folded shape to point the distal end portion 11 of the insertion portion 2 to the lower renal calyx BR close to the bladder UB side. Then, for example, when performing treatment that crushes a kidney stone, the operator needs to move the distal end portion 11 closer to a treatment site TP of the kidney stone and perform treatment on the treatment site TP.

When the above-described endoscope 1 is used in such a case, the operator pulls the operation lever 14a, for example, in a predetermined direction to point the insertion portion 2 into the lower renal calyx BR, and accordingly, the entire bending portion 12 bends so that the distal end portion 11 can be inserted into the lower renal calyx BR.

For example, when the bending portion 12 is bent by 180° approximately relative to the direction in which the insertion portion 2 is inserted, the bending portion 12 bends as illustrated in FIG. 10 so that the distal end portion 11 is pointed to the treatment site TP as illustrated in FIG. 10.

Conventionally, an operation for moving the distal end portion 11 closer to the treatment site TP has not been easy but has required time.

However, in the state illustrated in FIG. 10, the operation knob 14b can be operated to protrude the channel tube 16 in the distal end direction from the distal end surface 11d of the distal end portion 11.

Figure 11:
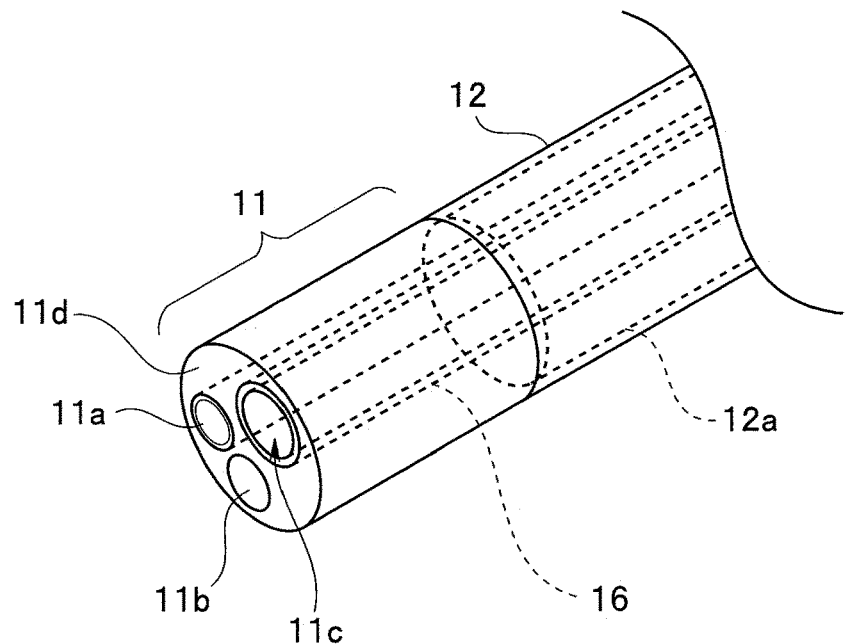
FIG. 11 is a perspective view of the distal end portion in a state in which the channel tube is not protruding from a distal end surface at the distal end portion according to the first embodiment of the present invention.
Figure 12:
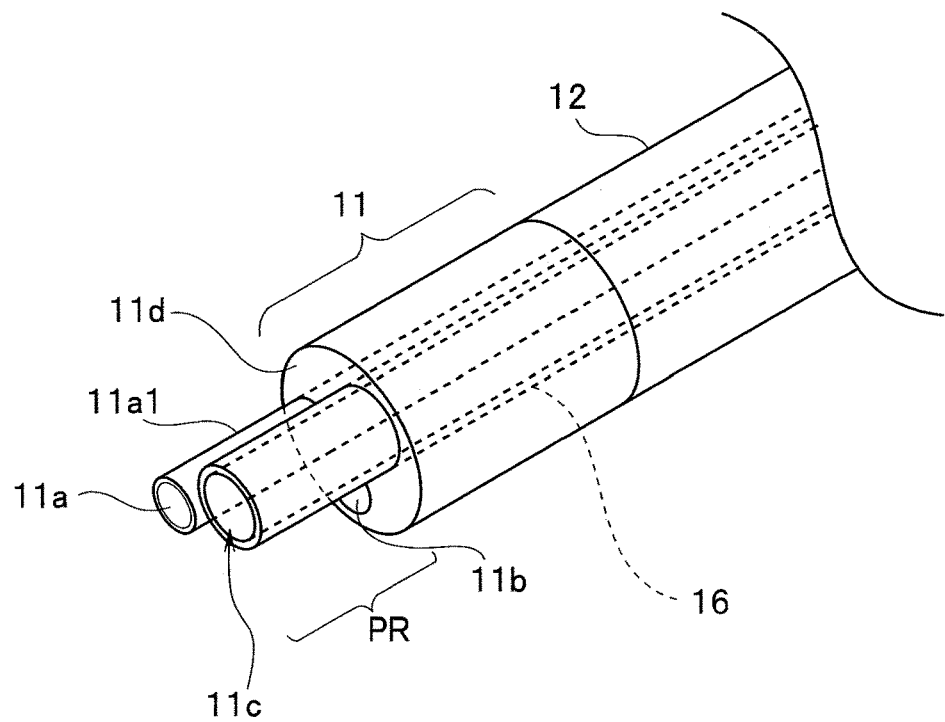
FIG. 12 is a perspective view of the distal end portion in a state in which the channel tube is protruding from the distal end surface at the distal end portion according to the first embodiment of the present invention.

FIG. 11 is a perspective view of the distal end portion 11 in a state in which the channel tube 16 is not protruding from the distal end surface 11d of the distal end portion 11. FIG. 12 is a perspective view of the distal end portion 11 in a state in which the channel tube 16 is protruding from the distal end surface 11d of the distal end portion 11.

As the user operates the operation knob 14b after moving the distal end portion 11 close to the treatment site TP as illustrated in FIG. 10, the channel tube 16 protrudes from the distal end surface 11d of the distal end portion 11 as illustrated in FIG. 12. As the channel tube 16 moves in the distal end direction of the longitudinal axis, the image guide 11a1 moves together with the channel tube 16 in the distal end direction of the longitudinal axis by the connecting member 17. Accordingly, as the channel tube 16 protrudes from the distal end surface 11d of the distal end portion 11, the image guide 11a1 protrudes from the distal end surface 11d of the distal end portion 11 as well.

In FIG. 12, a part protruding from the distal end surface 11d in the distal end direction of the central axis CO of the bending portion 12 configures a protrusion portion PR. Specifically, the protrusion portion PR includes the observation window 11a that is at least part of the distal end portion 11 and configured such that at least light for image pickup of the subject is incident on the observation window 11a, and the treatment instrument opening 11c configured such that a treatment instrument protrudes from the treatment instrument opening 11c, and the protrusion portion PR is movable in the distal end direction of the longitudinal axis OC of the bending portion 12.

As a result, the channel tube 16 forming the treatment instrument insertion channel 16a can also move closer to the treatment site TP as the observation window 11a moves closer to the treatment site TP. The user can cause the distal end of a laser probe of a laser medical treatment device to protrude, by operating the operation knob 14b, from the treatment instrument opening 11c to crush a kidney stone while the distal end portion 11 is close to the treatment site TP.

Thus, according to the above-described embodiment, it is possible to provide an endoscope capable of moving an observation window and a treatment instrument opening of an insertion portion into a largely bent tract.

In particular, through a simple operation, the user can move the distal end portion 11 of the insertion portion 2 into a largely bent tract and then move a treatment instrument closer to the treatment site TP.

Note that the bending portion 12 is bendable in the two directions UD and DD in the above-described embodiment, but may be bendable only in one direction. Specifically, only the bending wire 32a or the bending wire 32b may be inserted into the insertion portion 2.

For example, the operation lever 14a is connected with the bending wire 32a. As the operation lever 14a is operated to move in a predetermined direction, the bending wire 32a is pulled to the proximal end side. As a result, for example, the bending portion 12 is bendable only in the downward direction.

The following describes modifications of the first embodiment.

Note that in each modification below, a component same as a component of the endoscope 1 of the above-described embodiment is denoted by the same reference sign, and description thereof is omitted.

(Modification 1)

In the above-described embodiment, since the image guide 11a1 and the channel tube 16 are connected with each other through the connecting member 17, the image guide 11a1 moves to the distal end side as the channel tube 16 moves to the distal end side, but in the present Modification 1, the image guide 11a1 and the channel tube 16 are provided as one shaft body, and the operation knob 14b is operated to protrude the shaft body toward the distal end side from the distal end surface of the distal end portion 11.

Figure 13:
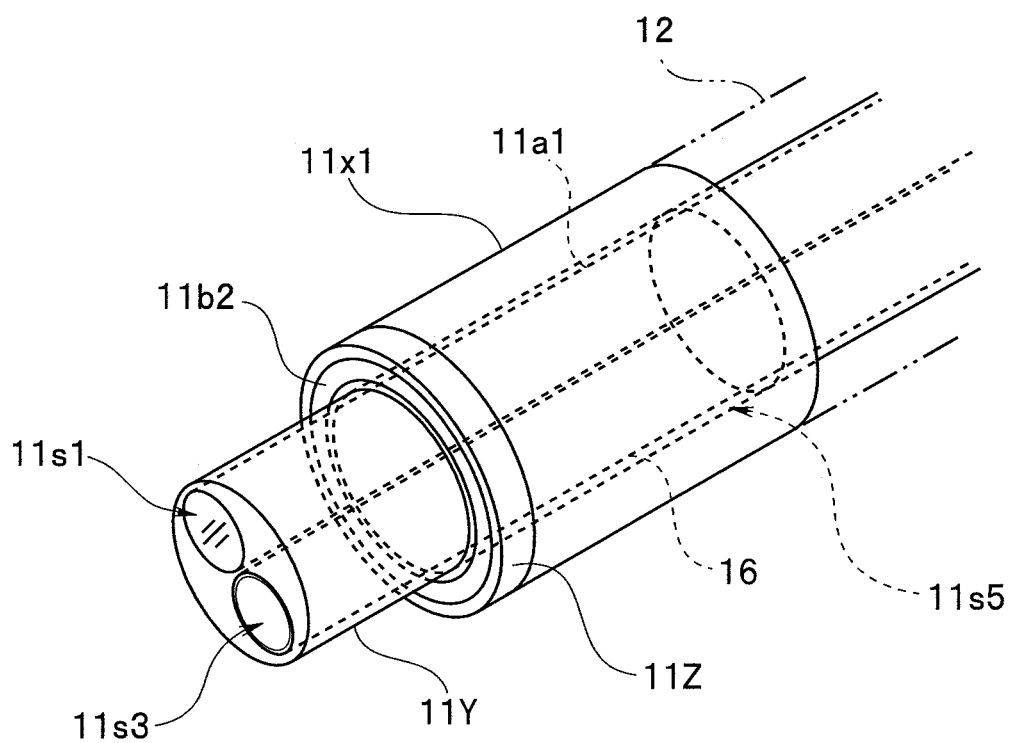
FIG. 13 is a perspective view of the distal end portion according to Modification 1 of the first embodiment of the present invention.

FIG. 13 is a perspective view of the distal end portion 11 according to the present Modification 1. The distal end portion 11 includes a distal end rigid member 11x1 of a cylindrical shape. FIG. 13 illustrates the bending portion 12 with dashed and double-dotted lines, and illustrates a state in which a shaft body 11Y including the image guide 11a1 and the channel tube 16 protrudes from the distal end surface of the distal end portion 11 at the distal end rigid member 11x1.

The shaft body 11Y is formed by shaping the image guide 11a1 and the channel tube 16 from resin material in a state in which the image guide 11a1 and the channel tube 16 are in parallel to each other. Accordingly, the shaft body 11Y has a circular sectional shape orthogonal to the central axis of the shaft body 11Y.

The image guide 11a1 and the channel tube 16 are inserted into the shaft body 11Y along the central axis of the shaft body 11Y. Specifically, in the shaft body 11Y, the elongated image guide 11a1 including the observation window 11a, and the treatment instrument insertion channel tube 16 including the treatment instrument opening 11c are formed as one elongated probe unit.

The distal end rigid member 11x1 is made of metal such as stainless steel and has a cylindrical shape. A distal end part of the shaft body 11Y is inserted into a hole 11s5 at the center of the distal end rigid member 11x1.

In addition, a ring illumination unit 11Z is provided on a distal end surface of the distal end rigid member 11x1. For example, an LED is disposed in an annular shape on a surface of the ring illumination unit 11Z on the distal end side. Illumination light is emitted from an annular illumination window 11b2 on the distal end side of the ring illumination unit 11Z.

The shaft body 11Y can protrude to the distal end side through a hole at the center of the ring illumination unit 11Z.

Thus, the shaft body 11Y can be inserted into the hole 11s5 of the distal end rigid member 11x1. As the shaft body 11Y as a probe unit moves in the hole 11s5, the observation window 11a and the treatment instrument opening 11c move in the distal end direction of the longitudinal axis of the bending portion 12. Accordingly, the distal end part of the shaft body 11Y as a probe unit configures a protrusion portion.

Thus, according to the present modification as well, effects same as the effects of the above-described embodiment are achieved, and shadow is unlikely formed on the subject since illumination light is emitted in an annular shape.

(Modification 2)

In the first embodiment and the Modification 1 described above, only the channel tube 16 and the image guide 11*a*1 protrude, but in the present Modification 2, the distal end portion 11 protrudes to the distal end side from the bending portion 12.

Figure 14:
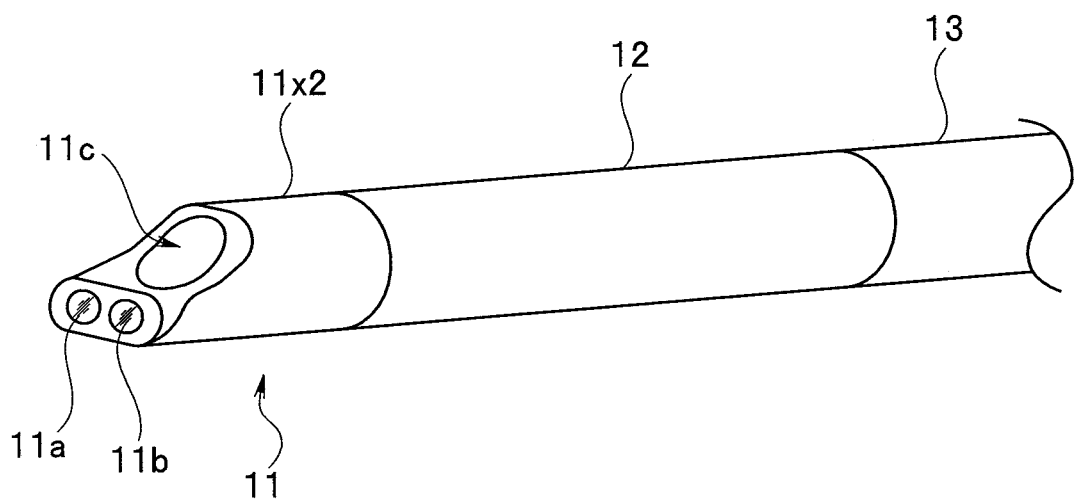
FIG. 14 is a perspective view of the distal end portion and the bending portion in a state in which the distal end portion is not protruding from the bending portion according to Modification 2 of the first embodiment of the present invention.
Figure 15:
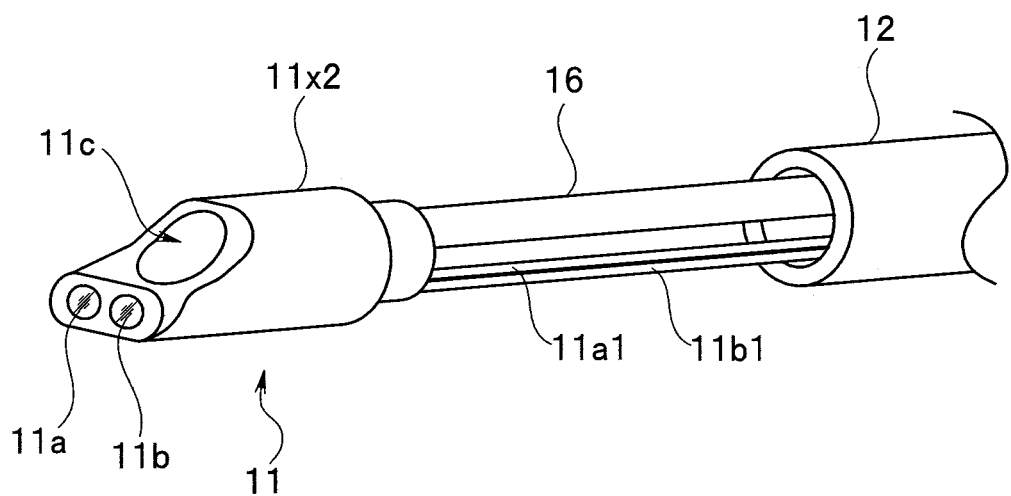
FIG. 15 is a perspective view of the distal end portion and the bending portion in a state in which the distal end portion is protruding from the bending portion according to the Modification 2 of the first embodiment of the present invention.

FIGS. 14 and 15 are perspective views of the distal end portion 11 and the bending portion 12 according to the present modification. FIG. 14 is a perspective view of the distal end portion 11 and the bending portion 12 in a state in which the distal end portion 11 is not protruding from the bending portion 12. FIG. 15 is a perspective view of the distal end portion 11 and the bending portion 12 in a state in which the distal end portion 11 is protruding from the bending portion 12. The distal end portion 11 includes a distal end rigid member 11*x*2. The distal end rigid member 11*x*2 is provided on the distal end side of the bending portion 12. The bending portion 12 and the flexible tube portion 13 are tubal members extended in the longitudinal axial direction of the insertion portion 2.

In the present modification, the distal end part of the image guide 11*a*1 as an image pickup unit, the distal end part of the light guide 11*b*1 as an illumination unit, and the distal end part of the channel tube 16 are inserted into the three holes 11*s*1, 11*s*2, and 11*s*3, respectively, formed in the distal end rigid member 11*x*2 and are fixed by a bonding agent or the like.

Specifically, the distal end parts of the image guide 11*a*1 including the observation window 11*a*, the treatment instrument insertion channel tube 16 including the treatment instrument opening 11*c*, and the light guide 11*b*1 including the illumination window 11*b* are held and fixed in the distal end rigid member 11*x*2.

Thus, as the operation knob 14*b* is operated, the distal end portion 11 protrudes in the distal end direction of the longitudinal axis of the bending portion 12 to separate from the bending portion 12. In the present modification, as the distal end portion 11 protrudes, the observation window 11*a*, the illumination window 11*b*, and the treatment instrument opening 11*c* protrude together in the distal end direction and move closer to a treatment site.

Specifically, as the channel tube 16 moves in the distal end direction of the longitudinal axis of the bending portion 12, the image guide 11*a*1 and the light guide 11*b*1 move together with the channel tube 16 in the distal end direction of the longitudinal axis.

Thus, the distal end portion 11 includes the observation window 11*a* configured such that at least light for image pickup of the subject is incident on the observation window 11*a*, and the treatment instrument opening 11*c* configured such that a treatment instrument protrudes from the treatment instrument opening 11*c*, and configure a protrusion portion movable in the distal end direction of the longitudinal axis of the bending portion 12. The protrusion portion includes the illumination window 11*b* for illuminating the subject.

As described above, as the distal end rigid member 11*x*2 moves relative to the bending portion 12 in the distal end direction of the longitudinal axial direction, the distal end rigid member 11*x*2 can change from a first state in which the distance between a proximal end surface of the distal end rigid member 11*x*2 and a distal end surface of the bending portion 12 is fixed to a first distance to a second state in which the distance between the proximal end surface of the distal end rigid member 11*x*2 and the distal end surface of the bending portion 12 is equal to a second distance longer than the first distance.

Specifically, the user can perform, by operating the operation knob 14*b* to move the distal end rigid member 11*x*2 relative to the bending portion 12 in the distal end direction of the longitudinal axial direction, movement from a first fixation position where the distal end rigid member 11*x*2 is fixed to the bending portion 12 to a second fixation position where the distal end rigid member 11*x*2 is separated further from the bending portion 12 than the first fixation position.

The distal end rigid member 11*x*2 is provided adjacent to the bending portion 12 in the first state. The distal end rigid member 11*x*2 is configured to separate from the bending portion 12 and move together with the channel tube 16 in the distal end direction of the longitudinal axial direction.

Part of the channel tube 16, part of the light guide 11*b*1, and part of the image guide 11*a*1 are exposed between the distal end rigid member 11*x*2 and the bending portion 12 in the second state.

Thus, according to the present modification as well, effects same as the effects of the above-described embodiment are achieved.

(Modification 3)

In the Modification 2 described above, the distal end portion 11 protrudes in the distal end direction of the longitudinal axis of the bending portion 12 to separate from the bending portion 12, but in the present modification, a tubal member that can extend and contract in the longitudinal axial direction of the bending portion 12 is provided between the distal end portion 11 and the bending portion 12, and the tubal member achieves a waterproof state in the bending portion 12 and the flexible tube portion 13.

Figure 16:
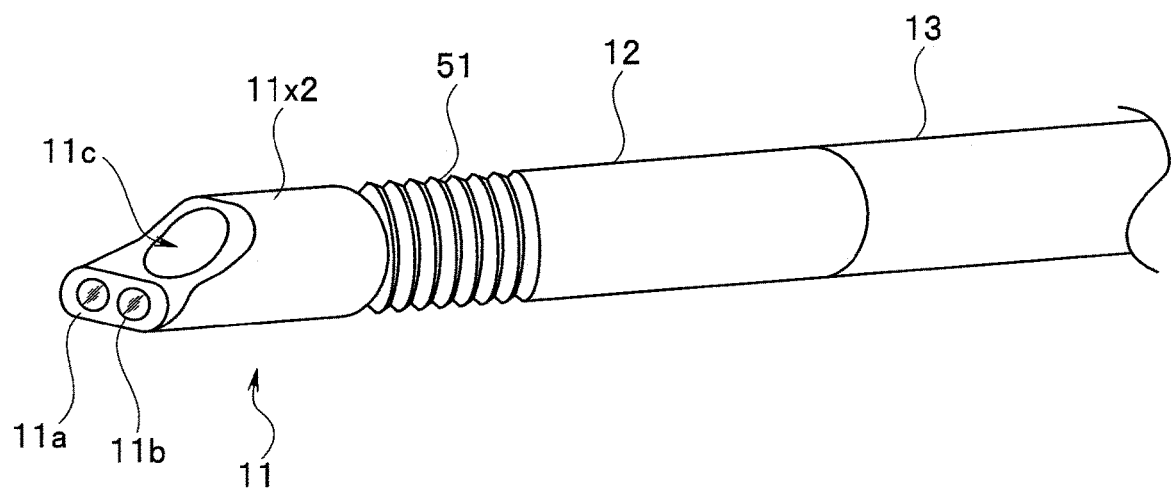
FIG. 16 is a perspective view of the distal end portion and the bending portion in a state in which the distal end portion is not protruding from the bending portion according to Modification 3 of the first embodiment of the present invention.
Figure 17:
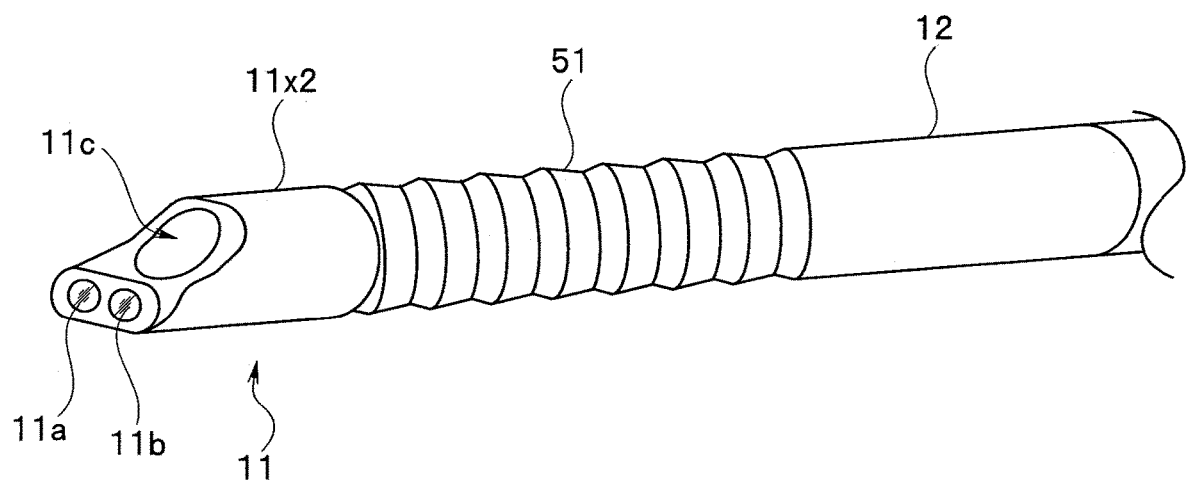
FIG. 17 is a perspective view of the distal end portion and the bending portion in a state in which the distal end portion is protruding from the bending portion according to the Modification 3 of the first embodiment of the present invention.

FIGS. 16 and 17 are perspective views of the distal end portion 11 and the bending portion 12 according to the present modification. As illustrated in FIGS. 16 and 17, an accordion member 51 as the tubal member is provided between the distal end portion 11 and the bending portion 12. FIG. 16 is a perspective view of the distal end portion 11 and the bending portion 12 in a state in which the distal end portion 11 is not protruding from the bending portion 12. FIG. 17 is a perspective view of the distal end portion 11 and the bending portion 12 in a state in which the distal end portion 11 is protruding from the bending portion 12.

The accordion member 51 is a tubal member that has a cylindrical shape and is extendable in the longitudinal axial direction of the bending portion 12. A distal end part of the accordion member 51 is fixed to a proximal end part of the distal end portion 11 by a bonding agent or the like. A proximal end part of the accordion member 51 is fixed to a distal end part of the bending portion 12 by a bonding agent or the like. The accordion member 51 is a link member fixed to the distal end rigid member 11*x*2 and the bending portion 12 in a waterproof manner to prevent ingress of liquid into the accordion member 51.

The accordion member 51 is extendable and contractable in the central axial direction of the bending portion 12. Specifically, the accordion member 51 is a link member provided between the distal end rigid member 11*x*2 and the bending portion 12 of the insertion portion 2 and extendable and contractable in the longitudinal axial direction. The image guide 11*a*1, the light guide 11*b*1, and the channel tube 16 are inserted inside the accordion member 51.

The accordion member 51 is contracted to a predetermined length in the longitudinal axial direction in the first state in which the distance between the proximal end surface of the distal end rigid member 11*x*2 and the distal end surface of the bending portion 12 is fixed to the first distance. The accordion member 51 is extended to a length longer than the predetermined length in the longitudinal axial direction in the second state in which the distance between the proximal end surface of the distal end rigid member 11x2 and the distal end surface of the bending portion 12 is equal to the second distance longer than the first distance.

When the distal end portion 11 is not protruding or is protruding from the bending portion 12, the accordion member 51 extends so that internal components in the bending portion 12 and the flexible tube portion 13 do not come into contact with liquid.

Thus, according to the present modification as well, effects same as the effects of the above-described embodiment are achieved, and internal components can be protected from liquid.

(Modification 4)

In the Modification 3 described above, the accordion member 51 that is extendable and contractable in the longitudinal axial direction of the bending portion 12 is provided between the distal end portion 11 and the bending portion 12, but in the present modification, the distal end portion 11 protrudes by a predetermined amount on the distal end side in the axial direction of the insertion portion 2 and then, the accordion member 51 bends in a predetermined direction.

Figure 18:
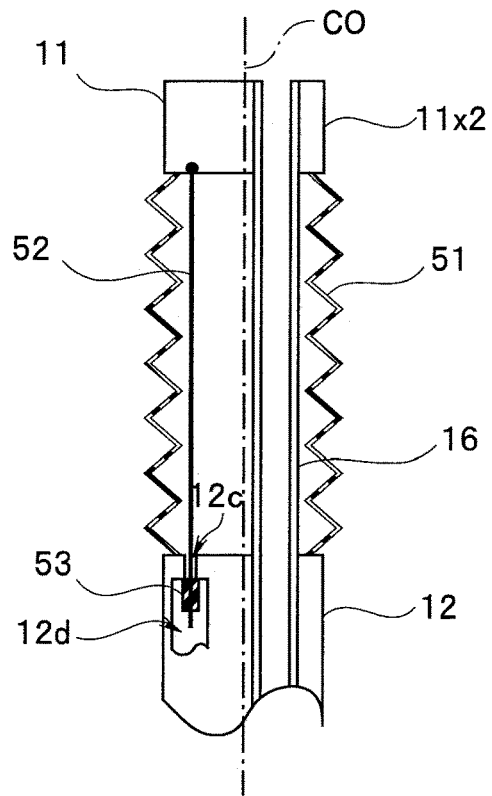
FIG. 18 is a cross-sectional view of a part including the distal end portion of the insertion portion according to Modification 4 of the first embodiment of the present invention.
Figure 19:
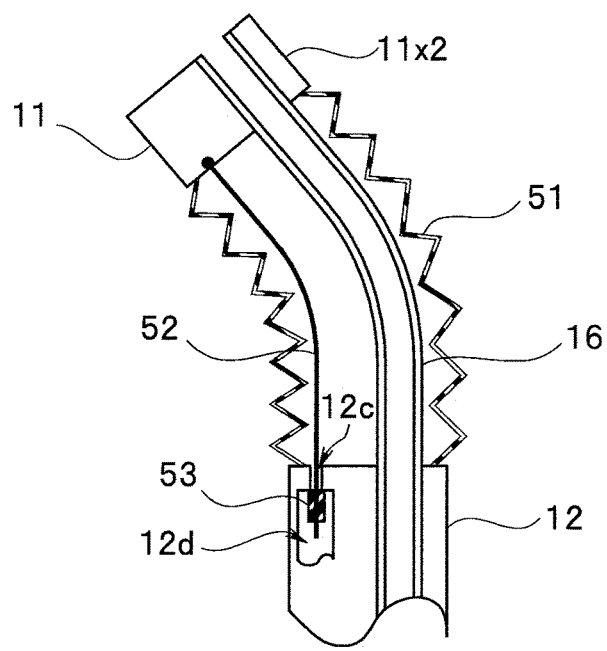
FIG. 19 is a cross-sectional view of the part including the distal end portion of the insertion portion according to the Modification 4 of the first embodiment of the present invention.

FIGS. 18 and 19 are cross-sectional views of a part including the distal end portion of the insertion portion 2 according to the present modification. FIGS. 18 and 19 illustrate a section along the longitudinal axial direction of the insertion portion 2, including the channel tube 16.

Note that although not illustrated in FIG. 18, the image guide 11a1 and the light guide 11b1 are inserted inside the accordion member 51.

The channel tube 16 is inserted into the insertion portion 2 and disposed off the central axis CO of the insertion portion 2 as illustrated in FIG. 18.

In addition, a metal wire 52 is inserted inside the accordion member 51. As illustrated in FIG. 18, the wire 52 as a linear member is disposed in the accordion member 51 as a tubal member and connects the distal end rigid member 11x2 and the bending portion 12.

The distal end of the metal wire 52 is fixed to the proximal end surface of the distal end rigid member 11x2 by a fixation such as a screw. The proximal end of the wire 52 is fixed to the distal end portion of the bending portion 12. In FIG. 18, a stop ring 53 is swaged and fixed to a proximal end portion of the wire 52. The stop ring 53 is disposed in a recess 12d provided in the bending portion 12 through a hole 12c provided in the bending portion 12.

The wire 52 is disposed in parallel to the central axis CO on a side opposite to the channel tube 16 with respect to the central axis CO of the insertion portion 2. The wire 52 is fixed to the distal end rigid member 11x2 and the bending portion 12 at a position shifted from the central axis of each of the distal end rigid member 11x2 and the bending portion 12.

The user can cause the distal end portion 11 to protrude, by operating the operation knob 14b in FIG. 1, in the distal end direction of the longitudinal axis of the insertion portion 2 to separate from the bending portion 12 as illustrated in FIG. 18. Since the channel tube 16, which is made of resin, has flexibility and also has rigidity to some extent, the distal end portion 11 separates from the bending portion 12 in the distal end direction of the longitudinal axis of the insertion portion 2.

The distal end portion 11 separates from the bending portion 12 in the distal end direction of the longitudinal axis of the insertion portion 2 until the wire 52 extends straight.

Thus, the accordion member 51 extends in the longitudinal axial direction until the wire 52 extends straight.

However, as the user further operates the operation knob 14b in FIG. 1 after the wire 52 extends straight, only part of the accordion member 51 opposite to the wire 52 with respect to the central axis of the accordion member 51 extends as illustrated in FIG. 19. As a result, the accordion member 51 bends on the wire 52 side relative to the central axis of the bending portion 12.

Specifically, the wire 52 configures a restrict member configured to restrict motion of part of the distal end rigid member 11x2.

Thus, after moving the distal end portion 11 close to a treatment site, the user can slightly move the distal end portion 11 closer to the treatment site by operating the operation knob 14b, and change the orientation of the distal end portion 11 by further operating the operation knob 14b, thereby performing observation and treatment.

As described above, according to the above-described embodiment and each modification, it is possible to provide an endoscope capable of moving an observation window and a treatment instrument opening of an insertion portion into a largely bent tract.

Second Embodiment

In the first embodiment, the insertion portion 2 includes the distal end portion 11 disposed on the distal end side of the bending portion 12, but in the present embodiment, the image guide 11a1, the light guide 11b1, and the channel tube 16 of the insertion portion 2 integrally protrude from a distal end side opening of the bending portion 12.

The endoscope of the present embodiment has a configuration substantially same as the configuration of the endoscope 1 of the first embodiment. Thus, in the present embodiment, a component same as a component of the endoscope 1 of the first embodiment is denoted by the same reference sign and description thereof is omitted, and the following description will be made on any different component.

Figure 20:
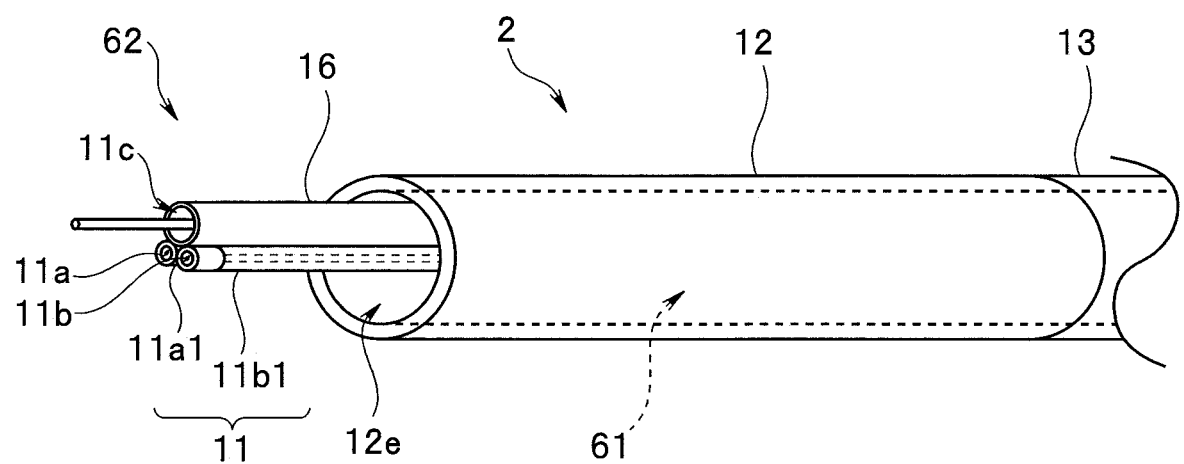
FIG. 20 is a perspective view of the bending portion of the insertion portion of an endoscope according to a second embodiment of the present invention.

FIG. 20 is a perspective view of the bending portion 12 of the insertion portion 2 of the endoscope 1 according to the present embodiment.

The bending portion 12 has the configuration illustrated in FIGS. 3 and 4. The inside of the bending portion 12 configures a liquid feeding conduit 61. Thus, when the insertion portion 2 is used in liquid such as normal saline, the inside of the bending portion 12 functions as a reflux path. The liquid feeding conduit 61 also communicates with the inner space of the flexible tube portion 13.

The image guide 11a1, the light guide 11b1, and the channel tube 16 are integrated by a bonding agent or the like in a bundle state in which the axial directions thereof are parallel to one another, and form an elongated probe 62. A distal end part of the probe 62 configures the distal end portion 11 of the insertion portion 2. The distal end portion 11 can protrude and retract from a distal end opening 12e of the bending portion 12.

Note that in the present embodiment as well, the image pickup unit may include the objective optical system and the image pickup device at the distal end. Similarly, the illumination unit may include the light-emitting element such as a light-emitting diode at the distal end. In this case, wires from the image pickup device and the light-emitting element are fixed to the channel tube 16 by a bonding agent or the like.

The user can cause a distal end portion of a laser probe to protrude from the treatment instrument opening 11c of the channel tube 16 and perform treatment.

Specifically, the distal end part of the probe 62 includes the observation window 11a configured such that at least light for image pickup of the subject is incident on the observation window 11a, and the treatment instrument opening 11c configured such that a treatment instrument protrudes from the treatment instrument opening 11c, and configures a protrusion portion that is movable in the distal end direction of the longitudinal axis of the bending portion 12.

In the protrusion portion, the image pickup unit including the observation window 11a, the illumination unit including the illumination window 11b, and the treatment instrument channel tube 16 including the treatment instrument opening 11c are connected together and protrude together through an operation of the operation knob 14b as an operation member.

The elongated probe 62 is inserted into the liquid feeding conduit 61 formed inside the flexible tube portion 13 and the bending portion 12.

Figure 21:
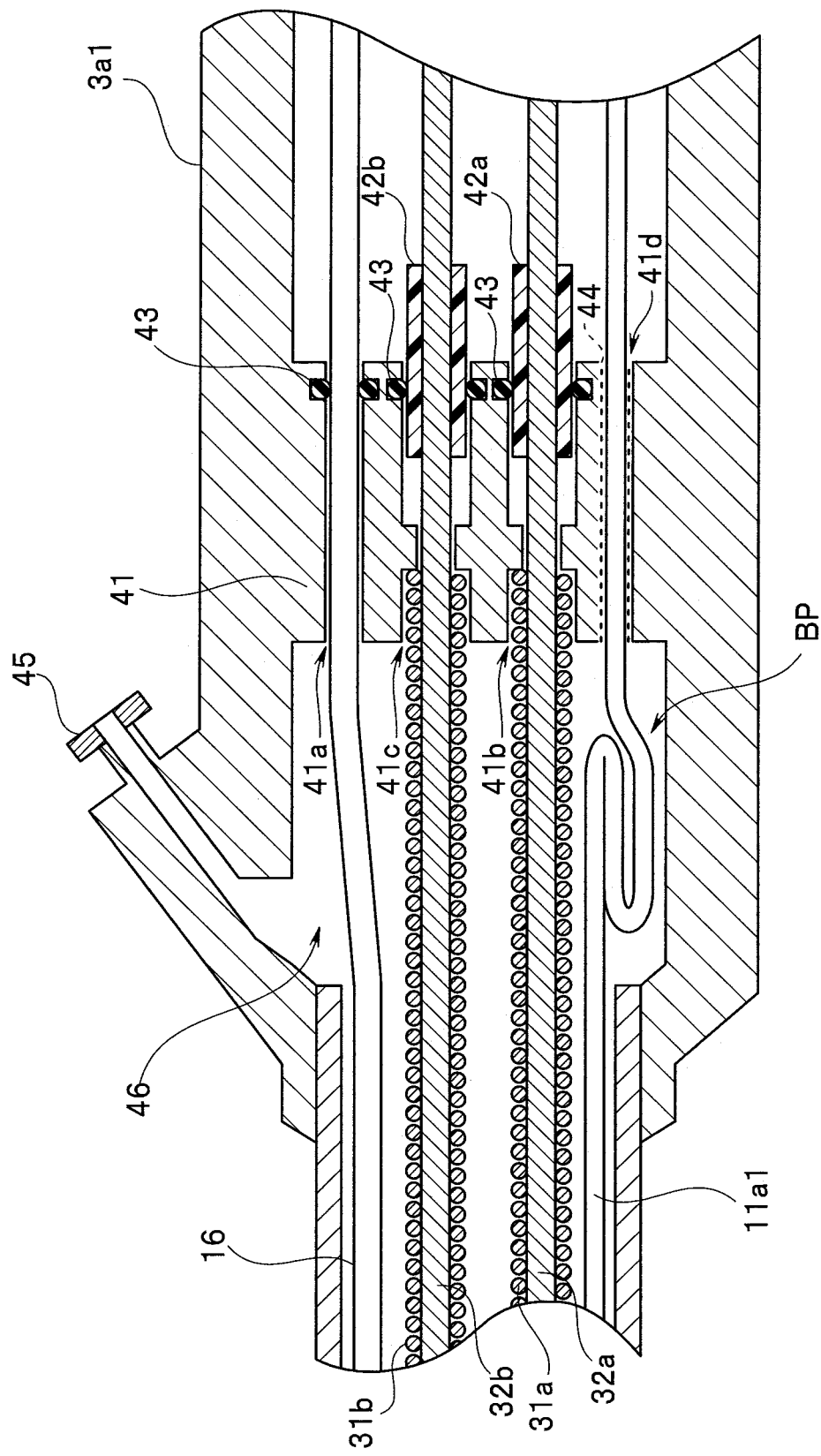
FIG. 21 is a cross-sectional view illustrating a fixed state of internal components in the operation portion according to the second embodiment of the present invention.

FIG. 21 is a cross-sectional view illustrating a fixed state of internal components in the operation portion 3. As illustrated in FIG. 21, a section along the longitudinal axis of the insertion portion 2 is indicated in the grasping portion 3a.

The internal structure of the operation portion 3 of the present embodiment is substantially same as the internal structure of the operation portion 3 of the first embodiment, and thus the following description will be made only on any different component.

The image guide 11a1, the light guide 11b1, and the channel tube 16 are separated from one another and inserted into the corresponding holes on the proximal end side of the probe 62.

A liquid feeding pipe sleeve 45 is provided to a grasping portion 3a1 according to the present embodiment. The liquid feeding pipe sleeve 45 is connected with a liquid feeding tube from a liquid feeding pump (not illustrated).

The liquid feeding pipe sleeve 45 communicates with an internal space 47 on the distal end side of the partition 41. The internal space 47 communicates with the liquid feeding conduit 61. The partition 41 separates the liquid feeding conduit 61 and an operation mechanism in the operation portion 3 from each other in a waterproof manner.

Thus, when liquid such as normal saline is fed from the liquid feeding pipe sleeve 45 to the internal space 47, the liquid ejects from the distal end opening of the bending portion 12.

The channel tube 16 is connected with the conversion mechanism 14c. Thus, as the channel tube 16 moves forward and backward along the central axis of the insertion portion 2 in accordance with a rotational operation of the operation knob 14b, the probe 62 protrudes and retracts from the distal end opening of the bending portion 12.

Thus, according to the above-described embodiment, it is possible to provide an endoscope capable of moving an observation window and a treatment instrument opening of an insertion portion into a largely bent tract.

In particular, through a simple operation, the user can move the distal end portion 11 of the insertion portion 2 into a largely bent tract and then move a treatment instrument closer to the treatment site TP.

The following describes Modification 5 of the second embodiment.

Note that in the modification below, a component same as a component of the endoscope 1 of the second embodiment described above is denoted by the same reference sign, and description thereof is omitted.

(Modification 5)

Figure 22:
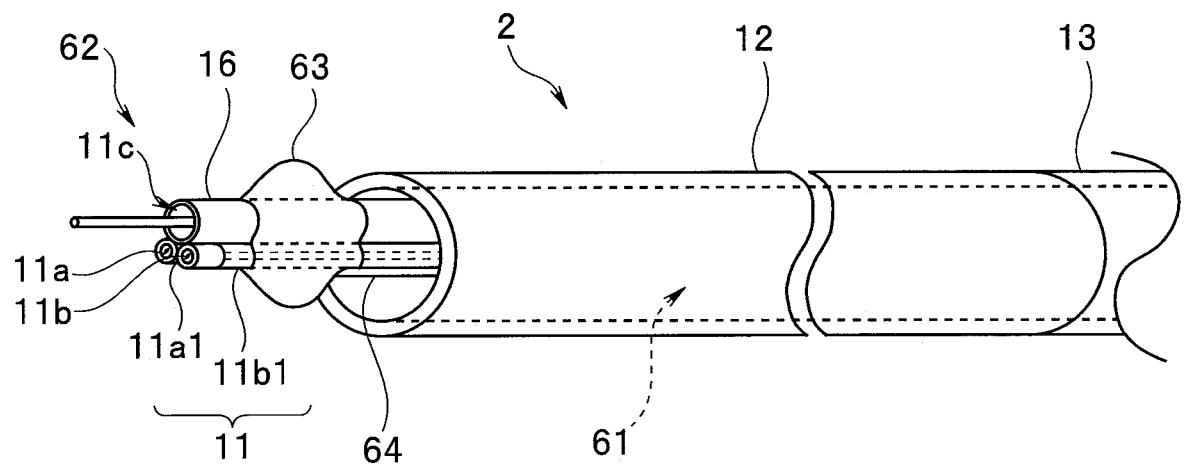
FIG. 22 is a perspective view of the bending portion of the insertion portion of the endoscope according to Modification 5 of the second embodiment of the present invention.

In the present modification, a balloon for expanding a narrowed part in a tract of the subject is provided to the distal end part of the probe 62 of the second embodiment described above. FIG. 22 is a perspective view of the bending portion 12 of the insertion portion 2 of the endoscope 1 according to the present modification.

Note that in the present modification, a component same as a component of the endoscope 1 of the second embodiment described above is denoted by the same reference sign, and description thereof is omitted.

A balloon 63 is fixed to the distal end part of the probe 62, surrounding the probe 62.

A water feeding tube 64 is connected with the balloon 63. The tube 64 is fixed to an outer peripheral surface of the probe 62 by a bonding agent or the like. A proximal end portion of the tube 64 is connected with a pump (not illustrated) capable of feeding normal saline.

When a narrowed part is found in a lumen of the subject during examination, the user can set the balloon 63 of the probe 62 in a gap of the narrowed part and then inflate the balloon 63 to expand the gap of the narrowed part.

Once the narrowed part is expanded, the probe 62 can be further moved into the lumen.

As described above, according to the embodiments and modifications described above, it is possible to provide an endoscope capable of moving an observation window and a treatment instrument opening of an insertion portion into a largely bent tract.

The following describes a modification common to the above-described embodiments and modifications.

According to the above-described embodiments and modifications, the observation window 11a and the treatment instrument opening 11c protrude in the distal end direction through an operation of the operation knob 14b, but the observation window 11a and the treatment instrument opening 11c may be manually caused to protrude in the distal end direction.

Figure 23:
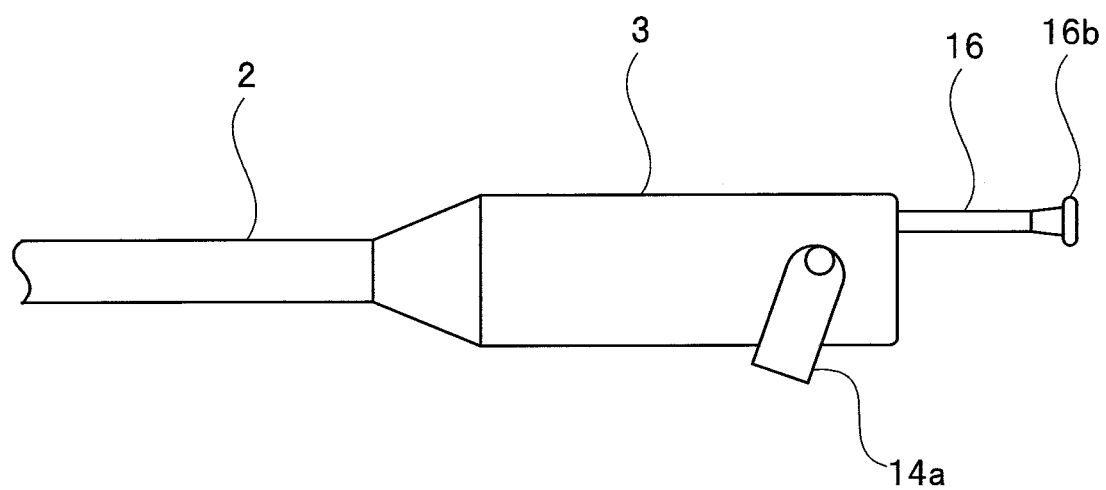
FIG. 23 is a front view of the operation portion according to a modification of the first and second embodiments of the present invention.

FIG. 23 is a front view of the operation portion 3 according to the present modification.

The operation portion 3 includes a hole (not illustrated) through which a proximal end portion of the channel tube 16 protrudes. A grasping portion 16b is provided to the proximal end portion of the channel tube 16.

The user can move the channel tube 16 along the longitudinal axis of the insertion portion 2 by grasping the grasping portion 16b with a hand and moving the grasping portion 16b in the longitudinal axial direction of the insertion portion 2.

Accordingly, the user can manually cause the observation window 11a and the treatment instrument opening 11c to protrude in the distal end direction of the longitudinal axis of the insertion portion 2.

The present invention is not limited to the above-described embodiments but may be, for example, changed or modified in various kinds of manners without departing from the gist of the present invention.

What is claimed is:

1. An endoscope comprising:
   an insertion portion extending in a longitudinal axis direction, the insertion portion comprising:
      a bending portion; and
      a distal end rigid body disposed distally relative to the bending portion, the distal end rigid body comprising an opening; and a channel tube extending proximally from the opening along the longitudinal axis direction;

wherein the distal end rigid body is configured to move together with a distal end of the channel tube relative to the bending portion in the longitudinal axis direction; and the distal end rigid body is movable between a first position where the distal end rigid body is at least indirectly coupled to the bending portion and a second position where the distal end rigid body separates further from the bending portion relative to the first position.

2. The endoscope according to claim 1, further comprising:

an operation portion disposed proximally relative to the insertion portion; and an operation knob provided to the operation portion and configured to move the channel tube relative to the bending portion in the longitudinal axis direction.

3. The endoscope according to claim 2, wherein the operation portion comprises a partition, the partition comprising a plurality of holes, the channel tube is inserted into one of the holes; and a seal is provided for sealing an outer surface of the channel relative to the one of the holes.

4. The endoscope according to claim 1, further comprising:

a light guide disposed in the insertion portion and configured to transmit illumination light; and an image guide disposed in the insertion portion and configured to transmit light of an object image, wherein the distal end rigid body holds a distal end part of the light guide including an illumination window and a distal end part of the image guide including an observation window, and as the channel tube moves relative to the bending portion in the distal end direction of the longitudinal axis direction, the light guide and the image guide moves with the channel tube in the distal end direction of the longitudinal axis direction.

5. The endoscope according to claim 4, further comprising:

an illumination optical system disposed distally relative to the light guide; and an objective optical system disposed distally relative to the image guide;

wherein the illumination window is disposed at a distal end part of the illumination optical system, and the observation window is disposed at a distal end part of the objective optical system.

6. The endoscope according to claim 4, wherein a part of the channel tube, a part of the light guide, and a part of the image guide are exposed between the distal end rigid body and the bending portion when the distal end rigid body separates from the bending portion and moves together with the distal end of the channel tube in the longitudinal axis direction.

7. The endoscope according to claim 4, wherein a part of the image guide is folded in an operation portion.

8. The endoscope according to claim 1, further comprising a link body provided between the distal end rigid body and the bending portion of the insertion portion, and the link body is configured to be extendable and contractable in the longitudinal axis direction;

wherein the link body is contracted to a predetermined length in the longitudinal axis direction in the first position and is extended to a length longer than the predetermined length in the longitudinal axis direction in the second position.

9. The endoscope according to claim 8, wherein the link body is a tubal accordion member.

10. The endoscope according to claim 8, further comprising a wire disposed in an interior of the link body and connecting the distal end rigid body and the bending portion, the wire being offset from a central axis of each of the distal end rigid body and the bending portion;

wherein the wire extending in the longitudinal axis direction in the first position and the second position; and the link body bends on a side of the wire in a third state in which the distal end rigid body moves radially relative to the central axis.

11. The endoscope according to claim 10, further comprising:

a stop fixed to a proximal end portion of the wire; and a recess having an opening is provided in the bending portion, the stop being disposed in the recess and the wire extending from the opening towards the distal end rigid body, wherein an outer diameter of the stop is larger than a width of the opening, a distal end surface of the stop contacts an inner surface of the opening of the recess in the third state.

12. The endoscope according to claim 1, wherein the distal end rigid body is configured to move between the first position in which a distance between a proximal end surface of the distal end rigid body and a distal end surface of the bending portion is a first distance and the second position in which the distance is a second distance longer than the first distance.

13. The endoscope according to claim 12, wherein the distal end rigid body is provided adjacent to the bending portion in the first position, the distal end rigid body is configured to separate from the bending portion and move with the channel tube in the distal end direction of the longitudinal axis direction, and part of the channel tube between the distal end rigid body and the bending portion is exposed in the second position.

14. The endoscope according to claim 12, wherein the distal end rigid body includes one of an interior annular surface or an exterior annular surface at a proximal side, the bending portion includes an other of the interior annular surface or the exterior annular surface at a distal side, and the interior annular surface is disposed within the exterior annular surface in the first position.

15. The endoscope according to claim 1, wherein an outer diameter of the distal end rigid body is larger than an inner diameter of the bending portion, the distal end rigid body is adjacent to the bending portion in the first position.

16. The endoscope according to claim 1, further comprising:

a link tube comprising a distal end portion and a proximal end portion, the distal end portion connected to the distal end rigid body, the proximal end portion connected to the bending portion, and the link tube being configured to be extendable and contractable in the longitudinal axis direction.

17. The endoscope according to claim 1, wherein an outer diameter of the distal end rigid body is larger than an inner diameter of the bending portion.

18. The endoscope according to claim 1, wherein
the distal end rigid body includes a first annular surface at a proximal side, and
the bending portion includes a second annular surface at a distal side.

19. An endoscope comprising:
an insertion portion extending in a longitudinal axis direction, the insertion portion comprises;
 a bending portion; and
 a distal end rigid body disposed distally relative to the bending portion, the distal end rigid body comprising an opening; and
a channel tube extending proximally from the opening along the longitudinal axis direction;
wherein the distal end rigid body is configured to move together with a distal end of the channel tube, and
the distal end rigid body is configured to move between a first position in which a distance between a proximal end surface of the distal end rigid body and a distal end surface of the bending portion is a first distance and a second position in which the distance is a second distance longer than the first distance.

* * * * *